United States Patent
McNulty, Jr.

(10) Patent No.: US 9,592,150 B2
(45) Date of Patent: Mar. 14, 2017

(54) MEDICAL DEVICE FOR THE TREATMENT OF HEMORRHOIDS, TISSUE INFLAMMATION AND OTHER CONDITIONS

(71) Applicant: William J. McNulty, Jr., Provo (TC)

(72) Inventor: William J. McNulty, Jr., Provo (TC)

( * ) Notice: Subject to any disclaimer, the term of this patent is extended or adjusted under 35 U.S.C. 154(b) by 402 days.

(21) Appl. No.: 14/163,538

(22) Filed: Jan. 24, 2014

(65) Prior Publication Data

US 2015/0209176 A1    Jul. 30, 2015

(51) Int. Cl.

| | |
|---|---|
| A61F 7/12 | (2006.01) |
| A61B 18/00 | (2006.01) |
| A61F 7/00 | (2006.01) |
| A61F 7/02 | (2006.01) |
| A61F 7/10 | (2006.01) |

(52) U.S. Cl.
CPC .......... *A61F 7/12* (2013.01); *A61B 2018/005* (2013.01); *A61F 2007/005* (2013.01); *A61F 2007/0261* (2013.01); *A61F 2007/108* (2013.01)

(58) Field of Classification Search
CPC .. A61F 7/12; A61F 7/005; A61F 7/105; A61F 7/0087; A61B 2018/005
See application file for complete search history.

(56) References Cited

U.S. PATENT DOCUMENTS

| | | | | |
|---|---|---|---|---|
| 3,939,842 A | * | 2/1976 | Harris | A61F 5/0093 607/113 |
| 4,227,535 A | * | 10/1980 | Connor | A61F 7/12 219/494 |
| 4,263,914 A | * | 4/1981 | Pawlak | A61H 21/00 601/112 |
| 4,331,151 A | * | 5/1982 | Golden | A61F 5/0093 607/105 |
| 4,563,182 A | * | 1/1986 | Stoy | A61F 5/0093 424/436 |
| 6,264,740 B1 | | 7/2001 | McNulty, Jr. | |
| 6,913,645 B2 | | 7/2005 | McNulty, Jr. | |
| 7,695,489 B2 | * | 4/2010 | Brockman | A61N 5/045 482/121 |
| 8,202,363 B2 | | 6/2012 | Wantling | |
| 2005/0177214 A1 | * | 8/2005 | Pohler | A61F 7/10 607/105 |
| 2007/0021809 A1 | * | 1/2007 | Cole | A61F 7/12 607/113 |

(Continued)

FOREIGN PATENT DOCUMENTS

WO    WO 0226311 A1 *  4/2002  ............ A61H 21/00

OTHER PUBLICATIONS

Barrett, Mike, "Home Remedies for Hemorrhoids—6 Natural Treatments", Feb. 19, 2013, Natural Society, http://naturalsociety.com/home-remedies-for-hemorrhoids-6-natural-treatments/.*

(Continued)

*Primary Examiner* — Joseph Stoklosa
*Assistant Examiner* — Nicole L Pobre
(74) *Attorney, Agent, or Firm* — Polsinelli PC

(57) ABSTRACT

This invention is directed to a medical device and a method of treating mammals, especially humans, to alleviate the symptoms, including pain, of several conditions and symptoms, including hemorrhoids, tissue inflammation and/or yeast infections, and open, draining wounds or incisions.

20 Claims, 2 Drawing Sheets

(56) References Cited

U.S. PATENT DOCUMENTS

| | | | | |
|---|---|---|---|---|
| 2007/0106109 A1* | 5/2007 | Ly | ............................ | A61H 19/44 |
| | | | | 600/38 |
| 2012/0059394 A1* | 3/2012 | Brenner | ............. | A61B 1/00087 |
| | | | | 606/142 |
| 2012/0225100 A1* | 9/2012 | Darcy | .................. | A61K 9/0056 |
| | | | | 424/400 |
| 2013/0023970 A1* | 1/2013 | Cull | .......................... | A61F 7/10 |
| | | | | 607/113 |

OTHER PUBLICATIONS

Instant BV Relief, "Get Rid of Bacterial Vaginosis with Apple Cider Vinegar", available Aug. 11, 2012, http://www.instantbacterialvaginosistreatment.com/bacterial-vaginosis-apple-cider-vinegar.html.*

* cited by examiner

MEDICAL DEVICE FOR THE TREATMENT OF HEMORRHOIDS, TISSUE INFLAMMATION AND OTHER CONDITIONS

FIELD OF THE INVENTION

This invention is directed to a medical device and a method of treating mammals, especially humans, to alleviate the symptoms, including pain, of several conditions and symptoms, including hemorrhoids, vaginal inflammation and/or yeast infections, and open, draining wounds or incisions.

BACKGROUND OF THE INVENTION

Prior to the invention disclosed herein, conditions such as hemorrhoids have been treated with topical applications, or suppositories. One of the leading medicaments is phenylephrine (rectal). However, while the relief provided by this medicament is only temporary, it can be contra-indicated if the patient has high blood pressure and/or heart disease, thyroid disease, diabetes, and can lead to side effects, such as skin problems, including acne. Hemorrhoids have also been treated surgically, but of course, that is a much more involved and expensive method of treatment, which many patients are reluctant to undergo. Hemorrhoids may exist in several forms, including external, thrombosed, prolapsed internal, internal or combined (internal and external).

Thus, there exists a need for temporary treatment and relief of the symptoms of hemorrhoids, without the contra-indications and side effects of phenylephrine (rectal) or the more invasive, expensive surgical treatment.

SUMMARY OF THE INVENTION

In one aspect, the invention provides a medical device that can be used by the consumer who may have one or more of high blood pressure or heart disease, diabetes, thyroid disease or for the relief of tissue inflammation. On the other hand, the medical device of the invention will not cause side effects, such as acne.

In yet other embodiments of the invention, there is provided a method of treating hemorrhoids, vaginal inflammation and/or yeast infections and draining open wounds or incisions.

According to one embodiment of the invention, a low cost tubular element, having high heat capacity, which has been chilled, as by refrigeration or other mechanism (e.g., ice bath), can be inserted into the anal canal and/or rectum, vagina, or an open wound or incision of the patient. The chilling effect will bring temporary relief of the symptoms of hemorrhoids, such as the itching, burning sensations, in a non-chemical manner. Thus, there is no likelihood of the inducement of side effects or the contra-indications for patients as those for phenylephrine (rectal) noted above. For use in the treatment of inflammation in the vagina or in draining wounds or incisions, the cooling effect will provide temporary relief of these symptoms/conditions as well.

The method of use of the medical device includes the chilling (by refrigeration, ice-bath, or otherwise) of the medical device, formed of the high heat capacity materials, and insertion/placement of the chilled medical device into the affected area.

These and other embodiments of the invention will become apparent when read in light of the following detailed description of the preferred embodiments in conjunction with the appended drawings.

DETAILED DESCRIPTION OF THE PREFERRED EMBODIMENTS

Figure 1:
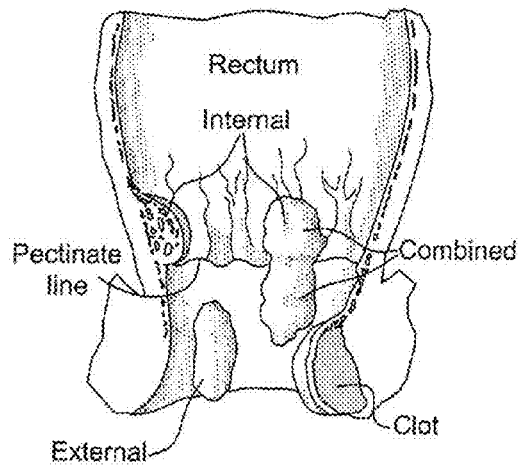
FIG. 1 is a schematic representation of typical hemorrhoids.

FIG. 1 illustrates various forms of hemorrhoids in the human patient. As can be seen from FIG. 2, the medical device 2, in its simplest form can take the shape of a cylindrical tube, have a generally cylindrical outer surface 4, with an aperture therein. The aperture could be a throughbore 6, but it is to be understood that the aperture may be drilled or bored through a mass of material, after forming the device, or formed from a combination of boring and broaching, such that non-circular apertures could be formed, or it could be created in other variations, such as elliptical during forming of the material by extrusion, molding and other shaping techniques. Thus, while the term "throughbore" is used to describe the aperture, it should be expressly understood that as used throughout the specification and claims, both circular, flat-sided, and non-circular cross-sections of the aperture are encompassed by the term "throughbore".

Figure 2:
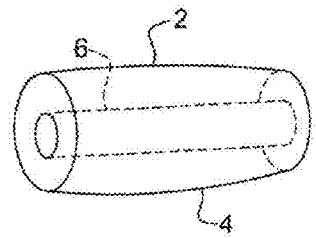
FIG. 2 is a schematic representation of the medical device of the invention in its most basic form.

The throughbore 6 is most conveniently placed along the center axis of the device 2 as seen in FIG. 2, but such placement is not essential and it may occupy a position other than that of a central axis of the device 2 as seen in FIG. 2.

Figure 3:
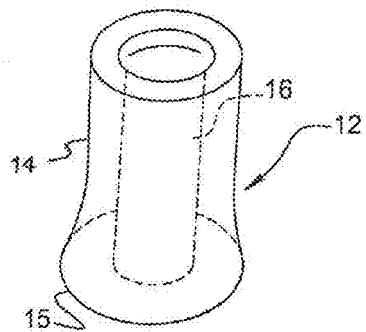
FIG. 3 is a schematic representation of a medical device of the invention in another embodiment.

FIG. 3 illustrates a second embodiment of the medical device in which device 12 has a general frusto-conical shaped outer surface 14 with a flared end 15. As in FIG. 2, a throughbore 16 is most conveniently placed along the center axis of the device 12, but such is not essential as noted above.

Figure 4:
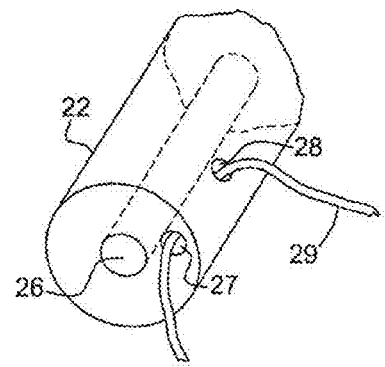
FIG. 4 is a schematic representation of the medical device of the invention with a bail or string to aid in removal of the device after use.

FIG. 4 illustrates a third variant of the medical device 22 of the invention having an aperture having an opening 27 in an end face thereof, with the other end of the opening 28 existing in a lateral surface thereof to accommodate a string 29 (or plastic-coated fine wire or high strength plastic, such as dental floss) to aid in removal of the device 22 after use. As with the embodiments of FIGS. 2 and 3, it has a throughbore 26.

Figure 5:
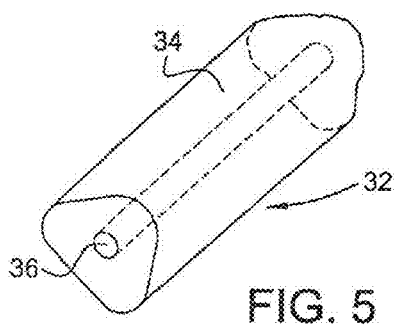
FIG. 5 is a further schematic representation of the medical device of the invention having a cross-sectional configuration which is triangular.

FIG. 5 is a further variation of the medical device 32 of the invention having an external surface 34 of a shape such that a cross-section thereof is triangular. As with the embodiments of FIGS. 2-4, it has a throughbore 36.

Figure 6:
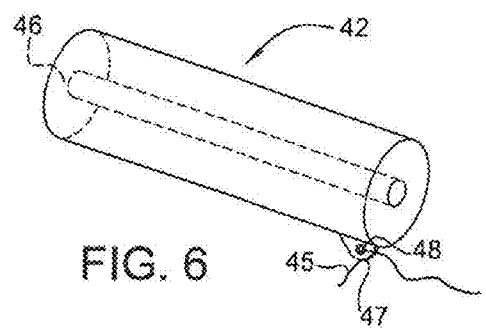
FIG. 6 is a schematic representation of a medical device of the invention having at least one protuberance, which could contain an aperture in the form of an eye, to retain the bail or string to assist in removal of the medical device after use.

FIG. 6 illustrates a further embodiment of the medical device 42, which includes a protuberance 47 on an outer surface of the device 42. The protuberance 47 preferably takes the form of a notch therein, or has an aperture 48 therein. The purpose of the aperture 48 (or notch) is to secure a bail 45, such as a string, plastic coated fine wire, or similar material, such as the plastic used for dental floss, as an aid for removing the used device 42.

Figure 7:
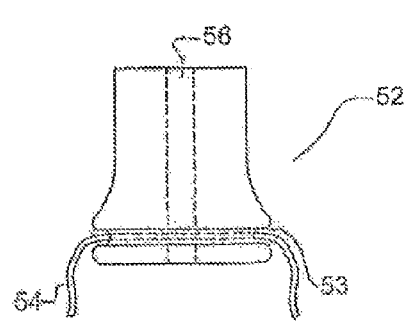
FIG. 7 is a further variant having a groove at the proximal (nearer the external) end of the medical device when inserted for use to attach a bail or string to aid in removal of the device.

FIG. 7 is a further variant of the medical device 52 having a groove 53 at the proximal end of the device 52. The purpose of groove 53 is to secure a bail 54 to aid in removal of the device 52 after use.

Figure 8:
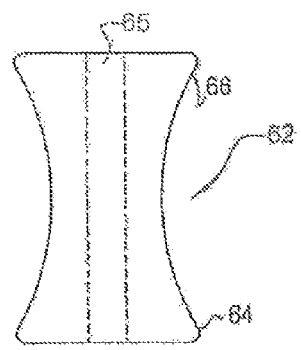
FIG. 8 is a still further variant of the shape of the medical device having flared proximal and distal edges.

FIG. 8 is a still further variant of the shape of device 62 having flared proximal 64 and distal 66 edges, which may, in some patients, be more comfortable to retain in position while the chilled device 62 engages in heat transfer with the hemorrhoids. The embodiments of FIGS. 6-8 all have throughbores.

The throughbores in FIGS. 6, 7 and 8 are respectively numbered as 46, 56 and 65 in these figures.

Figure 9:
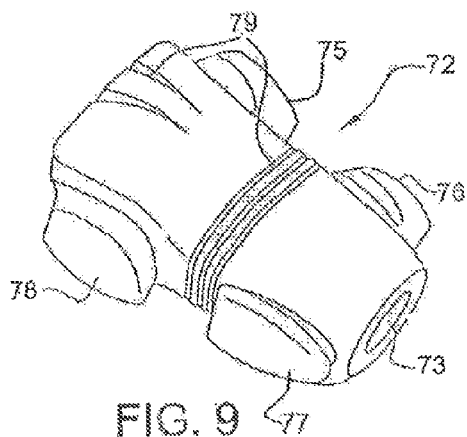
FIG. 9 is a still further variant of the medical device of the invention, having an overall frusto-conical shape, but with numerous protuberances and surface striations.

FIG. 9 is a still further variant of the medical device 72 of the invention, having an overall frusto-conical shape, but with numerous protuberances 75-78 and surface striations 79. As with the other embodiments, the device 72 has a throughbore 73. Although the surface striations are introduced with this embodiment, it is to be understood that the surface striations may appear in any of the embodiments disclosed herein, even though omitted from some drawing figures for purposes of clarity. The spacing of these surface striations is schematic, and they may take various forms such as being spaced $1/64$ of an inch apart. Alternatively the surface striations can be $1/32$; $3/64$; $1/16$; $5/64$; $6/64$; $7/64$; $1/8$; $9/64$, etc. inches, or other increments, apart. The spacing of the surface striations may also be irregular, such that different spacing exists between adjacent striations. It is also to be understood that the striations may be formed as embossments or bumps (as in FIG. 9) or as grooves (as in FIG. 12). The purpose of these surface striations, which may be in the form of bumps, embossments, grooves or a roughened surface, is to assist with retention of the device in the body of the user or as a carrier for external ointments added thereon.

Figure 10:
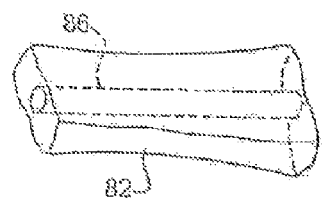
FIG. 10 is a still further variant in which the medical device has a rectangular cross-sectional shape with an aperture therethrough.

FIG. 10 is a still further variant in which the medical device 82 has a generally rectangular cross-sectional shape with rounded edges and is provided with a throughbore 86.

Figure 11:
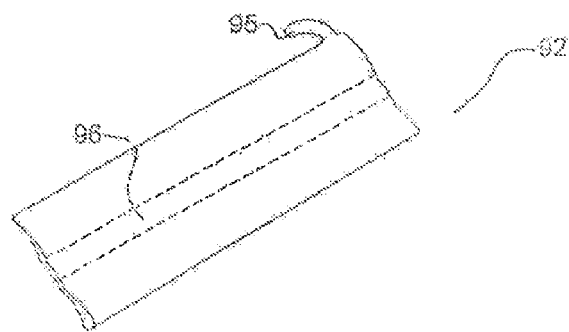
FIG. 11 is a schematic representation of a medical device of the invention having at least one protuberance, which could be in the form of a hook, to retain the bail or string to assist in removal of the medical device after use; and, FIG. 12 is a schematic representation of a further embodiment of the invention having a generally cross-sectional shape of a rectangle with curved corners, and further containing surface striations on its external surface, wherein this embodiment further contains a notch facilitating the attachment of a bail or string to aid in removal of the medical device after use.

FIG. 11 is a schematic representation of a medical device 92 of the invention having at least one protuberance, which could be in the form of a hook 95, to retain the bail or string (not shown) to assist in removal of the medical device after use. As with the other devices, device 92 has a throughbore 96.

Figure 12:
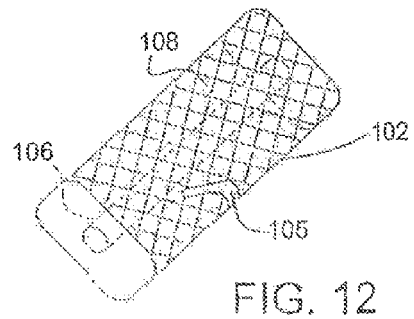

FIG. 12 is a schematic representation of a still further embodiment of the invention, where the medical device 102 of the invention has a generally rectangular cross-sectional shape with rounded corners. A notch 105 is provided along one rounded edge of the device to receive a bail, string, plastic coated fine wire, or other element, such as dental floss to aid in removal of the device 102 from the user. Similar to other embodiments of the invention, the device 102 contains a throughbore 106. A series of intersecting surface striations 108 covers at least opposed portions, but preferably all portions of outer surface of device 102. As described above, the spacing between surface striations is shown schematically in the drawings but can be selected from the group consisting of $1/64$; $1/32$; $3/64$; $1/16$; $5/64$; $6/64$; $7/64$; $1/8$; $9/64$, etc, inches, or other increments, apart. In this embodiment of the invention, the outer surface of the body 102 has surface striations, cross-hatching or roughened surface 108. The purpose of the modified surface 108 on device 102 can accommodate various surface agents, such as lubricants, local anesthetics, antibiotics, astringents, or medically active substances, such as vinegar (for treating yeast infections).

In addition to the cylindric, frusto-conical, flared, triangular shapes illustrated herein, the shapes can be generally rectangular with rounded edges, or irregular in shape.

The dimensions of the outer diameter and length of the invention will vary according to the specific method of treatment but typically may be as small as $1/2$ inch outer diameter and 2-7 inches in length.

In the most preferred use, the medical device of the invention is chilled (by refrigeration, ice bath or other techniques) to lower the temperature of the medical device. As heretofore described, the medical device is preferably formed from a high heat capacity material. Suitable material include artificial materials comprising a combination of hardened calcium carbonate/sodium carbonate materials, such as described in my previous U.S. Pat. Nos. 6,264,740 and 6,913,645 (each incorporated by reference in its entirety); natural materials, such as stone and jade; ceramics; rubbers; geo-polymers (such as described in U.S. Pat. No. 8,202,362, hereby incorporated by reference in its entirety); some composites of plastics/fillers; plastics/metal and metals and alloys. Geo-polymers are known to be based on inorganic materials. Cements are called geopolymeric cement because it contains geopolymer minerals, consisting of alkaline aluminosilicates, best known under the name of poly(sialate), poly(sialate-siloxo) and/or poly(sialate-disiloxo). The hardened calcium carbonate/sodium carbonate materials with a high sodium carbonate component have the advantage of breaking down in sewer/septic systems, and therefore are considered to be a preferred material for this invention.

In order to obtain the maximum effective time of use, the chilling should be to or at 32° F. (0° C.), or slightly above. Temperatures below the freezing point of water might induce thermal damage to the tissues surrounding the medical device of the invention and therefore should be avoided.

Chilling could be effective by placing a plurality of devices in a container having a fluid therein to simultaneously chill a plurality of the medical devices of the invention. The fluid can be vinegar, alcohol, wine, brine, an ice bath, witch hazel, and mixtures thereof, or other suitable liquid which does not freeze at the freezing point of water. Once properly chilled, a single device is selected and inserted, either by the patient or a medical practitioner, to provide immediate relief from the symptoms/conditions mentioned herein.

Alternatively, the medical devices of the invention could be individually packaged in foil packages surrounded by one of the fluids mentioned above, or in a material such as Benadryl, a lubricant, an astringent, a local anesthetic, an antibiotic, or other material, which packages can be chilled individually or as a group.

It will be understood that other variations, and uses, of the medical device of the present invention will be envisioned by those skilled in the art reading the present disclosure or viewing the drawings herein, and it is to be understood that all uses of the medical device of the invention are within the scope of the invention as defined by the appended claims.

I claim:

1. A medical device comprising a high heat capacity material in a form of a solid body; said body formed of a non-toxic material; said body comprising:
   a solid body formed of a high heat capacity material comprising a combination of hardened calcium carbonate/sodium carbonate materials;
   said solid body defining a throughbore therein, said throughbore extending from a first end of the solid body to an end of the solid body distal from said first end; the solid body defining an external surface formed of the same high heat capacity material as the solid body, a cross-section of the body being a shape which is at least one shape selected from a group consisting of cylindric, frusto-conical, flared, triangular, rectangular, and irregular variations thereof;
   in which the body can be chilled in a range of temperatures down to 32° F. (0° C.) to impart heat transfer from a human body.

2. The medical device of claim 1, wherein the throughbore has a shape which is at least one selected from the group consisting of circular, non-circular and flat-sided shapes.

3. The medical device of claim 1, further comprising at least one protuberance on the external surface of the body, said protuberance defining an aperture for receiving at least one of a string, bail, plastic-coated fine wire or dental floss.

4. The medical device of claim 3, further comprising a string, bail, plastic-coated fine wire or dental floss in the aperture of the protuberance on the device.

5. The medical device of claim 1, further comprising an aperture to receive a string, bail, plastic-coated fine wire or dental floss.

6. The medical device of claim 1, further comprising a groove on the external surface of the body and at least one of a string, bail, plastic coated fine wire or dental floss in said groove.

7. The medical device of claim 1, further comprising a hook on the external surface of the body.

8. The medical device of claim 1, packaged in an individual, sealed foil container.

9. The medical device of claim 1, further comprising a series of striations on the external surface, the surface striations being spaced apart by at least 1/64 inch.

10. A kit comprising a plurality of the medical devices of claim 1, and a container to receive all of the plurality of devices, the container formed of a material suitable for chilling the medical devices in a range of temperatures down to approximately 32° F. (0° C.).

11. A method of draining an open wound or incision comprising inserting a chilled medical device according to claim 1 into an open wound or incision.

12. A method of treating a hemorrhoid comprising chilling a solid body formed of a high heat capacity material comprising a combination of hardened calcium carbonate/sodium carbonate materials, in a range of temperatures down to approximately 32° F. (0° C.); contacting the chilled body with the hemorrhoid, maintaining the chilled body in contact with the hemorrhoid for a period of time to effect heat transfer to the chilled body, and removing the body from contact with the hemorrhoid.

13. The method of claim 12, further comprising chilling the body in a fluid.

14. The method of claim 12, further comprising chilling the body in a fluid selected from the group consisting of brine, vinegar, alcohol, wine, witch hazel and mixtures thereof.

15. The method of claim 12, wherein the body contains a throughbore therein.

16. The method of claim 12, wherein the body is packaged in a sealed foil package, and the method further comprises chilling the package and the body, and thereafter opening the package and retrieving the chilled body.

17. A method of treating vaginal inflammation comprising chilling a solid body formed of a high heat capacity material comprising a combination of hardened calcium carbonate/sodium carbonate materials in a range of temperatures down to approximately 32° F. (° C.); inserting the chilled body into the vagina, maintaining the chilled body in contact with the vagina for a period of time to effect heat transfer to the chilled body, and removing the body from the vagina.

18. The method of claim 17, wherein the body is chilled in a fluid selected from vinegar, wine and mixtures thereof in a range of temperatures down to approximately 32° F. (0° C.) prior to being inserted into the vagina.

19. A method of treating a hemorrhoid comprising effecting a temperature change from ambient temperature of a solid body formed of a high heat capacity material comprising a combination of hardened calcium carbonate/sodium carbonate materials; contacting the solid body with the hemorrhoid, maintaining the solid body in contact with the hemorrhoid for a period of time to effect heat transfer between the solid body and the hemorrhoid, and removing the solid body from contact with the hemorrhoid.

20. A method of treating inflammation of human tissue comprising effecting a temperature change from ambient temperature of a solid body formed of a high heat capacity material comprising a combination of hardened calcium carbonate/sodium carbonate materials; contacting the solid body with a human tissue inflammation, maintaining the solid body in contact with the tissue inflammation for a period of time to effect heat transfer between the solid body and the tissue inflammation, and removing the solid body from contact with the tissue inflammation.

* * * * *